United States Patent
Rhodes et al.

(10) Patent No.: US 11,441,092 B2
(45) Date of Patent: Sep. 13, 2022

(54) COATING SOLUTIONS, COATINGS FORMED THEREFROM, AND COATED MEDICAL DEVICES

(71) Applicant: BioInteractions Ltd., Reading (GB)

(72) Inventors: Alan Rhodes, Wokingham (GB); Bethany Sheila Huddart, Didcot (GB)

(73) Assignee: BIOINTERACTIONS LIMITED, Reading (GB)

( * ) Notice: Subject to any disclaimer, the term of this patent is extended or adjusted under 35 U.S.C. 154(b) by 318 days.

(21) Appl. No.: 15/777,983

(22) PCT Filed: Nov. 24, 2016

(86) PCT No.: PCT/GB2016/000209
§ 371 (c)(1),
(2) Date: May 22, 2018

(87) PCT Pub. No.: WO2017/089739
PCT Pub. Date: Jun. 1, 2017

(65) Prior Publication Data
US 2018/0258363 A1 Sep. 13, 2018

(30) Foreign Application Priority Data
Nov. 24, 2015 (GB) ...................................... 1520751

(51) Int. Cl.
| | |
|---|---|
| *C10M 107/42* | (2006.01) |
| *A61L 29/08* | (2006.01) |
| *C10M 169/04* | (2006.01) |
| *C10M 173/00* | (2006.01) |
| *C08F 226/10* | (2006.01) |
| *A61L 29/14* | (2006.01) |
| *C09D 5/00* | (2006.01) |
| *C09D 139/06* | (2006.01) |
| *C10M 149/18* | (2006.01) |

(Continued)

(52) U.S. Cl.
CPC ......... *C10M 107/42* (2013.01); *A61L 29/085* (2013.01); *A61L 29/14* (2013.01); *C08F 226/10* (2013.01); *C09D 5/00* (2013.01); *C09D 139/06* (2013.01); *C10M 149/18* (2013.01); *C10M 169/041* (2013.01); *C10M 169/044* (2013.01); *C10M 173/00* (2013.01); *A61L 2400/10* (2013.01); *A61L 2420/02* (2013.01); *A61L 2420/06* (2013.01); *B05D 1/18* (2013.01); *B05D 3/06* (2013.01); *C10M 2201/02* (2013.01); *C10M 2207/0215* (2013.01); *C10M 2209/04* (2013.01); *C10M 2209/084* (2013.01); *C10M 2209/0845* (2013.01); *C10M 2209/104* (2013.01); *C10M 2209/12* (2013.01); *C10M 2215/086* (2013.01); *C10M 2215/10* (2013.01); *C10M 2215/22* (2013.01); *C10M 2217/024* (2013.01); *C10M 2217/028* (2013.01); *C10M 2217/0285* (2013.01); *C10M 2217/044* (2013.01); *C10M 2217/045* (2013.01); *C10N 2040/50* (2020.05); *C10N 2050/02* (2013.01); *C10N 2050/08* (2013.01); *C10N 2070/00* (2013.01)

(58) Field of Classification Search
CPC .......... C08J 133/04; C08L 39/06; A61L 29/00
See application file for complete search history.

(56) References Cited

U.S. PATENT DOCUMENTS

| | | | | |
|---|---|---|---|---|
| 7,838,110 | B2 * | 11/2010 | Zhu ...................... | C07D 203/08 428/345 |
| 2003/0203991 | A1 | 10/2003 | Schottman et al. | |

(Continued)

FOREIGN PATENT DOCUMENTS

| | | |
|---|---|---|
| CA | 1297215 C | 3/1992 |
| CN | 85109215 A | 9/1986 |

(Continued)

OTHER PUBLICATIONS

Katime et al., Swelling Properties of New Hydrogels Based on the Dimethyl Amino Ethyl Acrylate Methyl Chloride Quatemary Salt with Acrylic Acid and 2-Methylene Butane-1, 4-Dioic Acid Monomers in Aqueous Solutions, Materials Science and Applications, 2010, 1, pp. 162-167 (Year: 2010).*
Egyptian Office Action issued in counterpart EG 2018050853, dated May 4, 2021 with English Language translation of relevant portions.
A. Dean Sherry, Ph.D. et al."A primer on gadolinium chemistry." J Magn Reson Imaging. Dec. 2009 :30(6): 1240-1248. Doi:10.1002/jmri.21966.
English Language translation of Chinese Office Action and search report issued in counterpart application No. CN 201680079911.5 dated Aug. 26, 2021.

*Primary Examiner* — Dah-Wei D. Yuan
*Assistant Examiner* — Andrew J Bowman
(74) *Attorney, Agent, or Firm* — Charles C. Achkar; Ostrolenk Faber LLP

(57) ABSTRACT

A method of making a coating solution includes the steps of polymerising an initial monomer feed comprising an N-vinyl pyrrolidone and an acrylate, preferably methacrylate, salt in water to synthesise a copolymer thereof, acidifying the resulting copolymer-water mixture to give free carboxylic acid groups along the copolymer backbone, diluting the aqueous solution down with alcohol, and adding a cross-linking agent which is capable of reacting with the carboxylic acid groups and curing the copolymer at a later stage after the coating solution has been applied to a substrate and the copolymer coated thereon. Also disclosed are a coating solution in storage, a method of coating a substrate which is on, or is part of, a medical device or other article, a substrate, article or medical device having a coating so applied, and a coated medical device packaged in a hydration solution. The aqueous-alcoholic coating solution may be stored for an extended period, suitably for at least one month and desirably for substantially longer, without deteriorating.

21 Claims, No Drawings

(51) Int. Cl.
*C10N 40/00* (2006.01)
*C10N 50/02* (2006.01)
*C10N 50/08* (2006.01)
*C10N 70/00* (2006.01)
*B05D 1/18* (2006.01)
*B05D 3/06* (2006.01)

(56) References Cited

U.S. PATENT DOCUMENTS

| | | | |
|---|---|---|---|
| 2004/0143180 A1* | 7/2004 | Zhong | A61L 31/145 |
| | | | 600/410 |
| 2007/0166344 A1 | 7/2007 | Qu | |
| 2012/0059111 A1* | 3/2012 | Sandhu | A61L 27/34 |
| | | | 524/548 |

FOREIGN PATENT DOCUMENTS

| | | |
|---|---|---|
| CN | 144 245 8 A | 9/2003 |
| CN | 1934206 A | 3/2007 |
| JP | 2005523981 A | 8/2005 |
| JP | 2009523890 A | 6/2009 |
| JP | 2009525176 A | 7/2009 |
| JP | 2013539399 A | 10/2013 |
| WO | 9933344 A1 | 7/1999 |
| WO | WO 03054029 A1 | 7/2003 |
| WO | 2003093357 A1 | 11/2003 |
| WO | 2007084452 A2 | 7/2007 |
| WO | 2007089784 A2 | 8/2007 |
| WO | WO 2011/052304 A1 | 5/2011 |
| WO | 2012032283 A1 | 3/2012 |

* cited by examiner

COATING SOLUTIONS, COATINGS FORMED THEREFROM, AND COATED MEDICAL DEVICES

CROSS REFERENCE TO RELATED APPLICATIONS

The present application claims priority to PCT/GB2016/000209, filed Nov. 24, 2016, which claims priority to GB 1520751.7, filed Nov. 24, 2015, which are hereby incorporated by reference herein.

FIELD OF THE INVENTION

This invention concerns coating solutions and methods of making them, methods of coating with such solutions and coatings formed from the solutions, and medical devices or other articles provided with such coatings, but especially medical devices intended to be inserted into the human or non-human animal body. The invention more specifically concerns coatings for medical devices comprising lubricious polymers so as to enhance the properties of the devices when in contact with the body.

BACKGROUND OF THE INVENTION

Lubricious coatings for medical devices are intended to facilitate insertion, manipulation, articulation and removal of the device. Typical such devices are catheters and other tubes. It is common for such devices to be provided with a surface which is potertially lubricious, either by coating part or all of the device with a potertially lubricious coating material, or by manufacturing it from such a material. It is generally the case that immediately before insertion of such a device into the body, the potertially lubricious surface requires hydration, typically by immersing it in a sterile saline solution or water, in order to fully develop its lubricity.

It is desirable to be able to reliably store medical devices of this kind already in water or saline solution for an extended period, before use, for example in sealed ready-for-use bags or pouches. However, especially in relation to coated devices, this demands a stable and durable lubricious coating which will stand up to handling and storage during the time between packaging and use without appreciable deterioration in the coating or its lubricious properties.

Furthermore, current coating solutions for applying lubricious coatings to devices tend to be short-lived. Many coating solutions have a tendency to increase in viscosity over time, which is detrimental to consistert application in serial coating processes, and may even gel. Therefore, coating solutions need to be changed on a regular basis during use, which results in low production efficiency when a coating line needs to be interrupted to wash and refill a dip-tank, and high wastage.

Current lubricious coatings that need a cross-linking agent to be included in the coating solutions frequently require the cross-linker to be added just prior to use, and for additional cross-linker to be added during the production run to 'reactivate' the coating solution.

SUMMARY OF THE INVENTION

The elements of the invention which are the subject of this patent application include a method of making a coating solution, a coating solution made by the method, a coating solution in storage, a method of coating a substrate which is on, or is part of, a medical device or other article, a substrate, article or medical device having a coating so applied, a coated medical device packaged in a hydration solution, and a coated substrate, article or medical device wherein the coating has certain novel and advantageous features.

The invention addresses improvements in coating solutions, with the object of providing one or more of various advantages, which may include a coating solution with an extended pot-life (meaning both the storage life and the usage life of the coating solution); avoiding the need to mix in a cross-linker just prior to the application of the solution to a device; reduced frequency of having to discard and replace the coating solution during production; reduced waste; ease of use; and a stable coating after having been cured on the device that can be stored in water for extended periods of time, enabling the production of ready-to-use pre-hydrated products.

The various aspects of the invention specifically include those set out in the appended claims, and also include other aspects disclosed, mentioned and discussed in the following detailed description, as well as those set out in the specific Examples herein.

DETAILED DESCRIPTION

The method of making a coating solution includes the steps of polymerising an initial monomer feed comprising an N-vinyl pyrrolidone and an acrylate, preferably methacrylate, salt in water to synthesise a copolymer thereof, acidifying the resulting copolymer-water mixture to give free carboxylic acid groups along the copolymer backbone, diluting the aqueous solution down with alcohol, and adding a cross-linking agent which is capable of reacting with the carboxylic acid groups and curing the copolymer at a later stage after the coating solution has been applied to a substrate and the copolymer coated thereon.

The invention provides that during the time between adding the cross-linking agent and putting the solution to further use by applying it to the substrate, the aqueous-alcoholic solution may be stored for an extended period, suitably for at least one month and desirably for substantially longer.

It is to be understood that 'acrylate' here is used in its broad sense to mean substituted as well as unsubstituted derivatives of acrylic acid. Among the acrylate monomer salts that may be included for co-polymerisation with the selected N-vinyl pyrrolidone species are the salts of acrylic acid, methacrylic acid, 2-carboxyethyl acrylate, 2-carboxyethyl methacrylate, methacryloyl-L-lysine, mono-2-(methacryloyloxy)ethyl maleate. Among possible acrylate salts are barium methacrylate, lithium methacrylate, magnesium acrylate, sodium acrylate, zinc (di)methacrylate, sodium methacrylate, zinc acrylate, zirconium acrylate, potassium acrylate. Other salts include 3-sulfopropyl acrylate potassium salt, 3-sulfopropyl methacrylate sodium salt. Accordingly, suitable cations for the acrylate salts include lithium, sodium, potassium, magnesium, barium, and zinc, sodium being most generally preferred. Protected acrylic acids, namely acrylic anhydride, methacrylic anhydride, may also be included as co-monomers.

The initial monomer feed may specifically comprise from about 3 to 35% by weight, and preferably about 5 to about 25% by weight, of acrylate salt, based on the total monomer contert, to yield a suitable acid contert for the cross-linker to react with and stabilise the coating, without overly prejudicing the viscosity of the solution. For the purpose of consistertly calculating weight proportions, the acrylate salt is taken to be a sodium salt.

While the monomer species in the monomer feed may comprise solely an N-vinyl pyrrolidone, usually unsubstituted N-vinyl pyrrolidone and in many cases specifically 1-vinyl-2-pyrrolidone, and an acrylate, preferably methacrylate, salt, the copolymer may also include minor proportions of additional monomer species compatible with the storage and coating benefits of the invention. Any such additional monomer species should also be included in the initial monomer feed.

Such additional co-monomers may include vinyl acetate (to aid coating adhesion), acrylamide (to aid lubricity), glycerol methacrylate (to increase hydrophilicity), 2-hydroxyethyl methacrylate (to increase hydrophilicity), methoxy polyethylene glycol methacrylate (to increase lubricity and flexibility), polyethylene glycol methacrylate (to increase lubricity and flexibility), 2-methacryloyloxyethyl phosphorylcholine (to increase hydrophilicity). Zwitterionic co-monomers include [2-(methacryloyloxy)ethyl] dimethyl-(3-sulfopropyl)ammonium hydroxide, 2-((2-(methacryloyloxy)ethyl)dimethylammonio)ethyl 2-methoxyethyl phosphate, and 2-((2-(methacryloyloxy)propyl)dimethylammonio)ethyl 2-methoxyethyl phosphate.

Different combinations of co-monomers may be employed. Any additional monomers should not amount to more than 50% by weight of the total monomer mixture, and preferably not more than 40% by weight.

The co-polymerisation of the monomers is carried out under standard conditions, using a suitable initiator such as a radical initiator like an azo or peroxide initiator, which may be initiated by thermal (heat) or photo (UV or visible) initiation, as known in the art.

We have found it advantageous to synthesise the initial copolymer as a salt, but to cross-link it later in its acid form. We have found that polymerisation as the free acid (methacrylic acid for example) can lead to the formation of insoluble poly salts, whereby the poly(N-vinyl pyrrolidone) and poly(methacrylic acid) formed during the polymerisation form a poly salt together that precipitates out of solution. Thus, it is advantageous to form the co-polymer when the acid is present in its salt form. Conversion to the free acid is then required to enable cross-linking, otherwise no reaction with the cross-linker will occur. Acidification after polymerisation converts the synthesised copolymer salt to the free acid and generates sodium chloride as a by-product, which may be removed during purification. A preferred acid is hydrochloric acid, but many other acids are also feasible.

After acidification, the copolymer-water mixture is desirably purified by removal of unreacted monomer and low molecular weight components below, for example, 10,000 g mol$^{-1}$. To this end, the solution may be dialysed, or precipitated, to remove some, or substantially all, such low molecular weight species. The removal of unreacted monomer, oligomer and salts can be controlled by the molecular weight cut-off (MWCO) of the membrane used to carry out the dialysis. For example, a 12-14,000 g mol$^{-1}$ MWCO membrane can be used to suitably remove species below 10,000 g mol$^{-1}$.

After acidification and optional purification, the pH of the solution is desirably about 4.5 or lower, typically in the range of 3 to 4.5. A pH greater than 3.5 or 4.0 within this overall range could be acceptable, as could a pH of less than 4.0 or 3.5.

The aqueous mixture suitably has a copolymer concentration of at least about 4% and less than about 12%, preferably 5.0% or greater, and preferably 7.5% or less, all by weight.

The step of diluting the aqueous copolymer solution down with alcohol is then carried out so that the diluted solution comprises typically 1 part copolymer-water mixture to 1-6 parts, typically 2-4 parts, e.g. 3 parts, of alcohol. These relative proportions may be measured by weight, or may more conveniently be measured by volume. The alcohol may be isopropyl alcohol (IPA, 2-propanol) or other lower alkanol, for example a C1 to C5 alkanol, such as methanol, ethanol, propanol (1-propanol) or butanol (1-butanol, 2-butanol, tert-butanol), pentanol or mixtures thereof. Other water and/or alcohol miscible solvents may be present in minor proportions in the final coating solution.

The cross-linking agent may be selected from among many that are commercially available, and is preferably a multifunctional carbodiimide, or polycarbodiimide (that is, one having at least two reactive functional carbodiimide groups per molecule) which selectively reacts with carboxylic acid groups. Or it may be a multifunctional aziridine, or polyaziridine (that is, one having at least two reactive functional aziridine groups per molecule). This cross-linker enhances coating stability on the surface of a coated device. The preferred cross-linking agents, compared with alternatives such as isocyanates, are less sensitive to the presence of water and are able to achieve long pot-life times. Their reactivity means they can be heat-cured using a standard oven.

In the preparation of coating solutions in accordance with the invention, the balance between the concentration of the aqueous copolymer (more specifically the free acid contert) and the amount of cross-linker added should be such that a stable durable coating is achieved after subsequently coating an article and curing the coating thereon, whilst still maintaining an extended pot-life, meaning that the solution does not gel too quickly in storage before use. For example, if too much cross-linker is added, the coating will be extremely stable, but the coating solution will gel within a few days. Similarly, if the concentration of the aqueous polymer (free acid contert) is too high, then again a stable coating will be afforded, but the pot-life will be significantly reduced (will become too viscous to use). Therefore, it is important to maintain a balance. We have found that a concentration between 5.0 to 7.5% w/w for the aqueous copolymer works well (that is, 5.0 to 7.5% w/w of copolymer in water).

The cross-linker would typically be added in an amount of between 5.0 and 50% by weight relative to the copolymer, more preferably between 10 and 40% by weight.

The proportion of cross-linker to the free acid contert of the copolymer in each particular case will depend upon the specific cross-linker used. The concentration of the aqueous copolymer solution and the cross-linker contert are accordingly managed so as to maintain the stability of the coating solution over an extended storage period while preserving the lubricity and adhesion (durability) of coatings deposited therefrom and cured after such storage. The solution preferably has a solids contert of from about 1.0 to about 10 weight percent. A preferred minimum is about 1.5 weight percent. A preferred maximum is about 5.0 weight percent.

Additional method steps may include the addition of one or more further polymers to the aqueous-alcoholic copolymer mixture. These further polymers may be used to improve the film-forming properties and the overall coating stability. Such further polymers may include hydrophilic polyurethanes, e.g. polyether-based hydrophilic polyurethanes, examples of which are available commercially, and can be formulated in suitable solvents, such as water and isopropyl alcohol or other suitable solvents e.g. lower (C1-05) alkanols, including methanol, ethanol, propanol (for example 1-propanol, 2-propanol), butanol (for example 1-butanol, 2-butanol, tert-butanol), pentanol, and other water and/or alcohol miscible solvents, or mixtures thereof, such as 2-butanone, tetrahydrofuran, tert-butyl methyl ether, 1-methyl-2-pyrrolidone.

Other such further polymer additions may also include hydrophilic polymers such as poly(vinyl pyrrolidone), poly(ethylene glycol), poly(acrylamide), poly(vinyl alcohol), hyaluronic acid, poly(methyl vinyl ether), poly(methyl vinyl ether-alt-maleic acid), poly(methyl vinyl ether-alt-maleic anhydride), poly(acrylic acid), poly(N-vinyl pyrrolidone-co-4-benzoylphenyl methacrylate-co-methoxy polyethylene glycol methacrylate-co-butyl methacrylate) or any selection of mixtures thereof. These further polymers may be used to improve the lubricity and dry-out time of the coatings. Other cured coating properties that can be adjusted by the use of additional polymers in the coating solution include flexibility, durability, adhesion, compatibility, and colour, amongst others.

The foregoing further polymer additions are suitably made before a period of extended storage, though could be made later.

The aqueous-alcoholic coating solution afforded by the invention accordingly comprises a poly(N-vinyl pyrrolidone-co-acrylic, preferably methacrylic, acid) together with an effective proportion of a cross-linking agent, particularly a multifunctional carbodiimide, or polycarbodiimide, or multifunctional aziridine, or polyaziridine, it being noted that alternative species of N-vinyl pyrrolidones and alternative species of acrylates are envisaged. The alcohol content of the solution assists in solubilising the cross-linker and aiding in the coating process, e.g. depositing the coating onto the substrate. As noted above, the proportion of cross-linker added to the aqueous-alcoholic copolymer solution will depend on a number of factors, including the concentration of copolymer—the higher the concentration, the lower the amount of cross-linker required.

In coating solutions containing further polyurethane components, a hydrophilic polyurethane may typically be included in a weight proportion of about 1 part polyurethane to between 1.5 and 3 parts copolymer, more frequently 1.7 parts or more, or 2.5 parts or less, of copolymer per part of polyurethane, both dissolved in aqueous-alcoholic solution.

The further hydrophilic polyurethane may be present at an equal weight to four times the weight of the cross-linker, or from more than 1.5 times, or up to 3 times, the weight of the cross-linker.

A preferred coating solution contains the various components within the following ranges of percentages by weight:

| | |
|---|---|
| Poly(N-vinyl pyrrolidone-co-methacrylic acid) in water: | 15-30% |
| Hydrophilic polyurethane: | 0.4-1.4% |
| Isopropyl alcohol (IPA): | 60-80% |
| Water: | 3-10% |
| Hydrophilic polymer: | 0.2-5.0% |
| Polycarbodiimide cross-linker: | 0.15-0.5% |

Other components may be included, with corresponding adjustments to the percentages. Such components may include physical modifiers, for example wetting agents to enhance coating characteristics, as well as chemical modifiers and antimicrobial agents.

The invention provides that during the time between adding the cross-linking agent and putting the solution to further use by applying it to the substrate, the aqueous-alcoholic solution may be stored in a closed vessel, suitably for at least one month (30 days) and desirably for six months or more. During this period, and subject to appropriate protection from elevated temperatures, the solution remains usable for coating purposes. Suitable storage vessels may be of plastic such as high density polyethylene or polypropylene, and/or glass bottles and/or stainless steel or other containers, jerrycans, drums, typically containing from 1 L to 25 L of coating solution. During storage, the solution is desirably not exposed to temperatures above 40° C. for continuous periods longer than 7 days. Accordingly, the invention provides a coating solution, made by the methods of the invention, which has the property of remaining usable for applying coatings, without further adjustment, after storage in a closed vessel for at least 30 days at a temperature not exceeding 40° C.

The method of coating a substrate comprises applying a coating solution according to the invention to a substrate, evaporating the solution to leave an uncured polymer coating thereon, and curing the coating on to the substrate. Curing comprises cross-linking the copolymer, and is suitably achieved with heating, suitably in an oven or by microwave radiation, to an elevated temperature, for example between 40 and 100 degrees Celsius, usually between 60 and 80° C., for a suitable length of time, such as 0.25 to 5 hours, preferably 0.5 to 1.5 hours. In general, the curing time of a coating is related to temperature, so that many coatings can be cured in under 15 minutes if a temperature greater than 90° C. is employed. We have found that the main constraint is the underlying medical device itself and what maximum temperature it can withstand without damage, such as deforming or warping for example. Fast curing times are beneficial because production times can be reduced, so throughput can be increased.

The substrate may be a surface of a medical device, and may be the whole surface of the medical device. Devices include Foley catheters (latex, poly(urethane) and silicone), intermittert (urological) catheters (PVC and latex), PTCA (percutaneous transluminal coronary angioplasty) catheters, balloon catheters endotracheal tubes, rectal catheters, rectal cones, endoscopes, drainage catheters, dilators, introducer sheaths, intraocular lens inserters, tracheal dilators, cannulas, needles, orthopaedic implants and guidewires. The coating may be applied by standard techniques including dipping, spraying, painting, wiping, and rolling.

It has been found that, depending upon the formulation of the coating solution, from 1 to 12 months of pot life (storage life) for the solution can be achieved without a detrimental increase in solution viscosity or without the solution gelling, and that the solution remains usable during that period. The inconvenient need to add cross-linker just prior to or during use, or to repeatedly drain and re-fill the coating just prior to or during use, as can be the case with current coating solutions, may be reduced or wholly avoided by means of the invention, while still achieving a stable lubricious coating which is resistant to abrasion and delamination. The formulation can be adjusted to control and extend coating dry-out times.

Coated devices in accordance with the invention may be stored in hydration media including water or saline or other solutions, such as cleaning, disinfecting, antimicrobial or antibacterial solutions, for extended periods, making them especially suitable for ready-to-use and multi-use products including urological catheters. Accordingly, the invention extends to a packaged device having a lubricious coating in accordance with the invention stored in a hydration medium. The packaging may be selected from any packaging acceptable for containing the hydration medium and suitable for the device concerned. The device will normally be sealed into the packaging until it is required for use. Suitable packaging may include bags, pouches, foils, sleeves, envelopes, trays, sheaths, bottles, tubes, cartons and films.

Medical devices to which the coatings of the invention are intended to be applied are normally required to be sterile when they are used. Accordingly, the practice of the invention may include a sterilisation step. A coated device stored in a hydration medium should be sterile. Numerous means of sterilisation are known for use with medical devices; among those preferred for use with this invention are ethylene oxide sterilisation techniques, and gamma and electron beam irradiation.

Further aspects of the invention are disclosed below in a series of specific Examples, which include some identified as reference Examples for comparative purposes.

EXAMPLES

Examples 1 to 3 highlight the synthesis of the base polymer. They highlight the inclusion of additional monomer species, which are compatible with the storage and coating benefits of the invention. They also show a possible purification method, e.g. dialysis, and the typical concentrations obtained after acidifying and purifying.

Example 1

Synthesis of poly(N-vinyl pyrrolidone-co-acrylic acid)

This example demonstrates the synthesis of the base polymer.

To a 250 mL flask, fitted with a nitrogen ($N_2$) inlet, was added N-vinyl pyrrolidone (NVP) (27 g), water (100 g) and sodium acrylate (3 g). The mixture was heated to 70° C. whilst being purged with $N_2$. Once the temperature had reached 70° C., 2,2'-azobis(2-methylbutanenitrile) (AMBN) (0.1 g) (dissolved in 1 g of NVP) was added in one portion to initiate the polymerisation. The polymerisation was carried out for 100 minutes, after which time water (100 g) containing HCl (50%) (4.5 mL) was added to quench the reaction and acidify the resulting copolymer-water mixture, thereby providing free carboxylic acid groups along the copolymer backbone. The mixture was allowed to stir and cool and was then purified by membrane dialysis against water (~10 L), using a molecular weight cut-off (MWCO) of 12-14,000 g $mol^{-1}$, for approximately 16 hours. Following dialysis, the final co-polymer solution had a concentration of 6.4% w/w and a pH of 4.4, thus indicating that the copolymer-water mixture was successfully acidified.

Example 2

Synthesis of poly(N-vinyl pyrrolidone-co-methacrylic acid)

This example demonstrates the synthesis of the base polymer.

To a 250 mL flask, fitted with a $N_2$ inlet, was added NVP (27 g), water (100 g) and sodium methacrylate (3 g). The mixture was heated to 70° C. whilst being purged with $N_2$. Once the temperature had reached 70° C., AMBN (0.1 g) (dissolved in 1 g of NVP) was added in one portion to initiate the polymerisation. The reaction was carried out for 100 minutes, after which time water (100 g) containing HCl (50%) (4.5 mL) was added to quench the reaction and acidify the resulting copolymer-water mixture, thereby providing free carboxylic acid groups along the copolymer backbone. The mixture was allowed to stir and cool and was then purified by membrane dialysis against water (~10 L), using a molecular weight cut-off (MWCO) of 12-14,000 g $mol^{-1}$, for approximately 16 hours. Following dialysis, the final co-polymer solution had a concentration of 6.1% w/w and a pH of 4.5, thus indicating that the copolymer-water mixture was successfully acidified.

Example 3

Synthesis of poly(N-vinyl pyrrolidone-co-methacrylic acid-co-methoxy polyethylene glycol methacrylate)

This example demonstrates the synthesis of the base polymer, including an additional monomer.

To a 250 mL flask, fitted with a $N_2$ inlet, was added NVP (27 g), water (100 g), sodium methacrylate (3 g) and methoxy poly(ethylene glycol) methacrylate (MPEGMA) (1.5 g). The mixture was heated to 70° C. whilst being purged with $N_2$. Once the temperature had reached 70° C., AMBN (0.1 g) (dissolved in 1 g of NVP) was added in one portion to initiate the polymerisation. The reaction was carried out for 100 minutes, after which time water (100 g) containing HCl (50%) (4.5 mL) was added to quench the reaction and acidify the resulting copolymer-water mixture, thereby providing free carboxylic acid groups along the copolymer backbone. The mixture was allowed to stir and cool and was then purified by membrane dialysis against water (~10 L), using a molecular weight cut-off (MWCO) of 12-14,000 g $mol^{-1}$, for approximately 16 hours. Following dialysis, the final co-polymer solution had a concentration of 6.8% w/w and a pH of 4.5, thus indicating that the copolymer-water mixture was successfully acidified.

Examples 4 to 6 highlight how the polymers are formulated (mixed) with the cross-linker. Two types of cross-linker are given, multifunctional carbodiimide and multifunctional aziridine. Example 6 shows how the polymer can be formulated without cross-linker, which has been included to highlight the cross-linker requirement, i.e. that the coating is not stable (durable) if no cross-linker is added to the formulation.

Example 4

Formulation with Coss-Linker, Multifunctional Polycarbodilmide

This example demonstrates how the base polymer is mixed with a carbodiimide cross-linker.

The co-polymer solution prepared in Example 2 (20 g) was mixed with isopropyl alcohol (IPA) (60 mL) and stirred until homogenous. To this was added multifunctional polycarbodiimide cross-linker (0.4 g) and the solution was stirred until the cross-linker had dissolved (~30 minutes). The concentration of the solution was 2.0% w/w.

Example 5

Formulation with Cross-Linker, Polyfunctional Aziridine

This example demonstrates how the base polymer is mixed with an aziridine cross-linker.

The co-polymer solution prepared in Example 2 (20 g) was mixed with IPA (60 mL) and stirred until homogenous. To this was added trimethylolpropane tris(2-methyl-1-aziridine propionate) (0.3 g) and the solution was stirred until the cross-linker had dissolved (~30 minutes). The concentration of the solution was 1.9% w/w.

Example 6

Formulation Without Cross-Linker

This example demonstrates how the base polymer is mixed with alcohol (no cross-linker).

The co-polymer solution prepared in Example 2 (20 g) was mixed with IPA (60 mL) and stirred until homogenous. The concentration of the solution was 1.5% w/w.

Examples 7 to 8 highlight the additional method step of adding one or more further polymers to the mixture, e.g. polyether-based hydrophilic and thermoplastic polyurethanes, which may be used to improve film-forming properties on certain substrates, thereby expanding the scope of materials that can be coated.

Example 7

Formulation Including Hydromed D640 (Commercially Available Product)

This example demonstrates how the additional polymer is formulated (added) to the base polymer formulation to provide a coating with enhanced film forming qualities.

Hydromed D640 (0.75 g) was dissolved in a mixture of IPA/water (50 mU6.25 mL). To this was added the co-polymer prepared in Example 2 (25 g) and the solution was mixed until homogenous (~30 minutes). Separately, multifunctional polycarbodiimide cross-linker (0.375 g) was dissolved in IPA (43.75 mL) and the mixture was added to the polymer solution and stirred for 2 hours. The final concentration of the solution was 2.5% w/w.

Example 8

Formulation Including HydroSlip C (Commercially Available Product)

This example demonstrates how the additional polymer is formulated (added) to the base polymer formulation to provide a coating with enhanced film forming qualities.

HydroSlip C (0.10 g) was dissolved in a mixture of IPA/water (10 mU1.25 mL). To this was added the co-polymer prepared in Example 2 (5 g) and the solution was mixed until homogenous (~30 minutes). Separately, multifunctional polycarbodiimide cross-linker (0.075 g) was dissolved in IPA (8.75 mL) and the mixture was added to the polymer solution and stirred for 2 hours. The final concentration of the solution was 2.3% w/w.

Examples 9 to 11 highlight further polymer additions that may include hydrophilic polymers, which may be used to improve the lubricity and dry-out time of the coatings.

Example 9

Formulation Including Hydrophilic Polymer, Poly(Vinyl Pyrrolidone)

This example demonstrates how the additional hydrophilic polymer is formulated (added).

Hydromed D640 (0.75 g) was dissolved in a mixture of IPA/water (50 mU6.25 mL). To this was added the co-polymer prepared in Example 2 (25 g) and the solution was mixed until homogeneous (~30 minutes). Separately, poly (vinyl pyrrolidone) (PVP) (0.75 g) was dissolved in IPA (32 mL). Once dissolved, this was added to the polymer solution previously prepared and mixed until homogenous. The cross-linker solution was prepared by dissolving multifunctional carbodiimide cross-linker (0.375 g) in IPA (11.75 mL). This was then added to the polymer mixture. The final solution was stirred for 2 hours. The concentration was 3.2% w/w.

Example 10

Formulation Including Hydrophilic Polymer, Poly(Ethylene Glycol)

This example demonstrates how the additional hydrophilic polymer is formulated (added).

Hydromed D640 (0.75 g) was dissolved in a mixture of IPA/water (50 mU6.25 mL). To this was added the co-polymer prepared in Example 2 (25 g) and the solution was mixed until homogeneous (~30 minutes). Separately, poly (ethylene glycol) (PEG) (0.5 g) was dissolved in IPA (32 mL). Once dissolved, this was added to the polymer solution previously prepared and mixed until homogenous. The cross-linker solution was prepared by dissolving multifunctional carbodiimide cross-linker (0.375 g) in IPA (11.75 mL) and then adding this to the polymer mixture. The final solution was stirred for 2 hours. The concentration was 3.0% w/w.

Example 11

Formulation Including Hydrophilic Polymer, Hyaluronic Acid

This example demonstrates how the additional hydrophilic polymer is formulated (added).

A 0.6% w/v solution of hyaluronic acid sodium salt (HA) was prepared by dissolving HA (0.6 g) in water (100 g). The co-polymer solution prepared in Example 2 (4 g) was combined with water (3 g) and the HA solution (3 g). IPA (14 mL) was added to this mixture dropwise under stirring such that a clear solution resulted. Hydromed D640 (0.15 g) was then dissolved in this mixture. Separately, the multifunctional carbodiimide cross-linker (0.057 g) was dissolved in IPA (1 mL) and then added to the coating solution. The solution was stirred for 2 hours. The concentration of the coating solution was 2.0% w/w.

Examples 12 to 15 highlight how the polymers/formulations prepared in the previous examples are coated onto various substrates/medical devices using various techniques, such as dipping or wiping and how they are cured using various temperatures/times.

Example 12

Coating of Formulation Prepared in Example 4 onto a PVC Intermittert Catheter Using a Dip Coating Technique This example demonstrates how the coating formulation prepared in Example 4 can be applied to a particular substrate/device and how it can be cured at a particular temperature for a particular period of time.

PVC Intermittert Catheters were first cleaned by wiping with an IPA soaked lint-free cloth. Once dry, they were dipped into the coating solution prepared in Example 4 and submerged for approximately 10 seconds. After this time, they were extracted and allowed to dry under ambient conditions for at least 10 minutes. They were then transferred to an oven and heated at 70° C. for 1 hour to cure the coating. The samples were allowed to cool before being packaged.

Example 13

Coating of Formulation Prepared in Example 6 onto a PVC Intermittert Catheter Using a Dip Coating Technique This example demonstrates how the coating formulation prepared in Example 6 (without cross-linker) can be applied to a particular substrate/device and how it can be heated at a particular temperature for a particular period of time. This example is included as a comparison to show the difference between a coating formulated with cross-linker and a coating formulated without cross-linker.

PVC Intermittert Catheters were first cleaned by wiping with an IPA soaked lint-free cloth. Once dry, they were dipped into the coating solution prepared in Example 6 and submerged for approximately 10 seconds. After this time, they were extracted and allowed to dry under ambient conditions for at least 10 minutes. They were then transferred to an oven and heated at 70° C. for 1 hour. The samples were allowed to cool before being packaged.

Example 14

Coating of Formulation Prepared in Example 7 onto a Silicone Foley Catheter Using a Dip Coating Technique This example demonstrates how the coating formulation prepared in Example 7 can be applied to a more challenging substrate through incorporation of an additional polyether-based polyurethane, which serves to improve the film-forming properties of the coating.

Silicone Foley Catheters were first cleaned by wiping with an IPA soaked lint-free cloth. Once dry, they were dipped into the coating solution prepared in Example 7 and submerged for approximately 15 seconds. After this time, they were extracted and allowed to dry under ambient conditions for at least 10 minutes. They were then transferred to an oven and heated at 70° C. for 1 hour to cure the coating. The samples were allowed to cool before being packaged.

Example 15

Coating of Formulation Prepared in Example 9 onto a PVC Intermittert Catheter Using a Dip Coating Technique This example demonstrates how the coating formulation prepared in Example 9 can be applied to a particular substrate/device and how it can be cured at a particular temperature for a particular period of time.

PVC Intermittert Catheters were first cleaned by wiping with an IPA soaked lint-free cloth. Once dry, they were dipped into the coating solution prepared in Example 9 and submerged for approximately 10 seconds. After this time, they were extracted and allowed to dry under ambient conditions for at least 10 minutes. They were then transferred to an oven and heated at 70° C. for 45 minutes to cure the coating. The samples were allowed to cool before being packaged.

Example 16

Coating of Formulation Prepared in Example 11 onto a Poly(Urethane) Catheter Using a Dip Coating Technique This example demonstrates how the coating formulation prepared in Example 11 can be applied to a particular substrate/device and how it can be cured at a particular temperature for a particular period of time.

Poly(urethane) catheters were first cleaned by wiping with an IPA soaked lint-free cloth. Once dry, they were dipped into the coating solution prepared in Example 11 and submerged for approximately 10 seconds. After this time, they were extracted and allowed to dry under ambient conditions for at least 10 minutes. They were then transferred to an oven and heated at 70° C. for 45 minutes to cure the coating. The samples were allowed to cool before being packaged.

Example 17

Coating of Formulation Prepared in Example 9 onto a Poly(Amide) PTCA Catheter Using a Wipe Coating Technique This example demonstrates how the coating formulation prepared in Example 9 can be applied to a particular substrate/device and how it can be cured at a particular temperature for a particular period of time.

Poly(amide) PTCA catheters were first cleaned by wiping with an IPA soaked lint-free cloth. Once dry, they were wipe coated using the solution prepared in Example 9 and allowed to dry under ambient conditions for at least 10 minutes. They were then transferred to an oven and heated at 65° C. for 1.5 hours to cure the coating. The samples were allowed to cool before being packaged.

Example 18

Coating of Formulation Prepared in Example 9 onto a Thermoplastic Elastomer (TPE) Based Catheter This example demonstrates how the coating formulation prepared in Example 9 can be applied to a particular substrate/device and how it can be cured at a particular temperature for a particular period of time.

Thermoplastic elastomer (TPE) based catheters was first cleaned by wiping with an IPA soaked lint-free cloth. Once dry, they were dipped into the coating solution prepared in Example 9 and submerged for approximately 10 seconds. After this time, they were extracted and allowed to dry under ambient conditions for at least 10 minutes. They were then transferred to an oven and heated at 95° C. for 8 minutes to cure the coating. The samples were allowed to cool before being packaged.

Examples 19 to 25 demonstrate the properties/functionality of the coated devices prepared in previous examples, such as reduced friction (increased lubricity), coating stability (durability), and increased dry-out time.

Example 19

Testing of Coated Example 12

The PVC catheters coated in Example 12 were evaluated for their coating uniformity using crystal violet dye, their lubricity after hydration in water for 20 seconds and coating durability using a wet glove test and subsequent dye. In all cases the coating was uniform, lubricious and durable under the test conditions employed. The coating demonstrated a dry-out time of approximately 3 minutes and a coefficient of friction below 0.3.

Example 20

Testing of Coated Example 13

The PVC catheters coated in Example 13 were evaluated for their coating uniformity using crystal violet dye, their lubricity after hydration in water for 20 seconds and coating durability using a wet glove test and subsequent dye. The uniformity and initial lubricity were adequate, however under mild abrasion the coating was easily removed from the surface of the catheter. Thus indicating the necessity for cross-linker to be added to the formulation.

Example 21

Testing of Coated Example 14

The silicone catheters coated in Example 14 were evaluated for their coating uniformity using crystal violet dye, their lubricity after hydration in water for 20 seconds and coating durability using a wet glove test and subsequent dye. In all cases the coating was uniform, lubricious and durable under the test conditions employed.

Example 22

Testing of Coated Example 15

The PVC catheters coated in Example 15 were evaluated for their coating uniformity using crystal violet dye, their lubricity after hydration in water for 20 seconds and coating durability using a wet glove test and subsequent dye. In all cases the coating was uniform, lubricious and durable under the test conditions employed. The coating demonstrated a dry-out time of approximately 6 minutes, i.e. twice as long as that shown by coated Example 12, as a result of the PVP inclusion. The coefficient of friction was typically below 0.2. Also, a cure time of 45 minutes was sufficient to provide the desired coating properties.

Example 23

Testing of Coated Example 16

The poly(urethane) catheters coated in Example 16 were evaluated for their coating uniformity using crystal violet dye, their lubricity after hydration in water for 20 seconds and coating durability using a wet glove test and subsequent dye. In all cases the coating was uniform, lubricious and durable under the test conditions employed. It was noted that the lubricity had increased in comparison with coated Example 12 as a results of the HA inclusion. The coefficient of friction was typically below 0.2. Also, a cure time of 45 minutes was sufficient to provide the desired coating properties.

Example 24

Testing of Coated Example 17

The poly(amide) catheters coated in Example 17 were evaluated for their coating uniformity using crystal violet dye, their lubricity after hydration in water for 20 seconds and coating durability using a wet glove test and subsequent dye. In all cases the coating was uniform, lubricious and durable under the test conditions employed.

Example 25

Testing of Coated Example 18

The TPE catheters coated in Example 18 were evaluated for their coating uniformity using crystal violet dye, their lubricity after hydration in water for 20 seconds and coating durability using a wet glove test and subsequent dye. In all cases the coating was uniform, lubricious and durable under the test conditions employed. Surprisingly, it was noted that the quality of the coating was akin to that achieved in coated Example 15, thereby highlighting that the desired coating properties can be achieved after a shorter curing period (8 minutes), when a higher cure temperature is employed.

Examples 26 to 27 demonstrate the increased pot-life of the coating formulations prepared in previous examples and include details of storage conditions, testing (e.g. viscosity), device coating and functional testing.

Example 26

Pot-Life Testing of the Formulation Prepared in Example 7

This example shows the comparative testing results for the formulation prepared in Example 7 tested on day 1 and after 9 months storage at ambient temperature.

| Time | Appearance | Concentration | Viscosity* |
| --- | --- | --- | --- |
| Day 1 | Clear, colourless solution | 2.48% w/w | 18 seconds |
| 9 months | Clear, colourless solution | 2.57% w/w | 22 seconds |

*viscosity has been measured using a Zahn Cup No. 2, which measures the time taken for the solution to flow through an orifice and can be used as a measure of viscosity. The relevant standards for this test method are ASTM D1084 and ASTM D4212.

After storage for 9 months, clean PVC Intermittert Catheters were dipped into the coating solution and submerged for approximately 10 seconds. After this time, they were extracted and allowed to dry under ambient conditions for at least 10 minutes. They were then transferred to an oven and heated at 70° C. for 1 hour to cure the coating. The samples were allowed to cool before being evaluated for their coating uniformity using crystal violet dye, their lubricity after hydration in water for 20 seconds and coating durability using a wet glove test and subsequent dye. In all cases the coating was uniform, lubricious and durable under the test conditions employed. Surprisingly, the performance of the coating was analogous to a sample coated with a freshly prepared solution, thereby highlighting the advantage of the present invention, to provide coating solutions with extended pot-life.

Example 27

Pot-Life Testing of the Formulation Prepared in Example 9

This example shows the comparative testing results for the formulation prepared in Example 9 tested on day 1 and after 6 months storage at ambient temperature.

| Time | Appearance | Concentration | Viscosity* |
|---|---|---|---|
| Day 1 | Clear, colourless solution | 3.23% w/w | 25 seconds |
| 6 months | Clear, colourless solution | 3.26% w/w | 31 seconds |

*viscosity has been measured using a Zahn Cup No. 2, which measures the time taken for the solution to flow through an orifice and can be used as a measure of viscosity. The relevant standards for this test method are ASTM D1084 and D4212.

After storage for 6 months, clean PVC Intermittert Catheters were dipped into the coating solution and submerged for approximately 10 seconds. After this time, they were extracted and allowed to dry under ambient conditions for at least 10 minutes. They were then transferred to an oven and heated at 70° C. for 1 hour to cure the coating. The samples were allowed to cool before being evaluated for their coating uniformity using crystal violet dye, their lubricity after hydration in water for 20 seconds and coating durability using a wet glove test and subsequent dye. In all cases the coating was uniform, lubricious and durable under the test conditions employed. Surprisingly, the performance of the coating was analogous to a sample coated with a freshly prepared solution, thereby highlighting the advantage of the present invention, to provide coating solutions with extended pot-life.

Example 28 demonstrates sterilisation (by ethylene oxide) and subsequent biocompatibility testing of a device coated with a formulation of the invention.

Example 28

EtO Sterilisation and ISO10993 Testing of a Coated PVC Catheter

A coating formulation was prepared according to a similar procedure as that described in Example 9. PVC Intermittert Catheters were then coated according to a similar procedure as that described in Example 15. The coated samples were sterilised by ethylene oxide (EtO) gas and then tested according to ISO10993, whereby the cytotoxicity, irritation, acute systemic toxicity and sensitisation effects of the coated article were evaluated. The coating was considered non-cytotoxic to the subconfluent monolayer of L-929 mouse fibroblast cells and non-irritant to the skin of New Zealand White Rabbits. It was also demonstrated that the coating did not reveal any systemic toxicity when administered to Swiss Albino mice and was non-sensitising to the skin of Guinea pigs under the experimental conditions and doses employed.

Example 29 demonstrates the stability of the coating when a coated device is left submerged in water for an extended period of time, i.e. the functionality is unaltered after this period. This is to exemplify the potertial for this coating to be utilised on ready-to-use (pre-hydrated) products.

Example 29

Long-Term Stability of Coated Device Stored (Sealed) in Water

A coating formulation was prepared according to a similar procedure as that described in Example 7. PVC Intermittert Catheters were then coated according to a similar procedure as that described in Example 15. Coated catheters were tested on day 1 and demonstrated a uniform, lubricious and stable (durable) coating. The coated catheters were then incubated in a sealed tube containing water at ambient temperature and tested periodically to determine the long-term stability of the coating.

| Duration of Incubation | Lubricious | Stable |
|---|---|---|
| 1 day | YES | YES |
| 6 months | YES | YES |
| 12 months | YES | YES |
| 18 months | YES | YES |

Unexpectedly, the samples incubated for 18 months still compared extremely well with a freshly coated catheter with regards to coating uniformity, lubricity and stability (durability). Thus demonstrating the long-term stability of the coating of the invention when incubated in water at ambient temperature.

Example 30

Increased Dry-Out Time of Coated Device Hydrated for an Extended Period

This example demonstrates that the dry-out time of the coating can be extended further by hydrating the coating for longer periods of time, e.g. 24 hours. This may be particularly advantageous for ready-to-use products supplied in water or saline, for example.

A coating formulation was prepared according to a similar procedure as that described in Example 9. PVC Intermittert Catheters were then coated according to a similar procedure as that described in Example 15. Coated catheters were tested on day 1 after being hydrated for 20 seconds. The coated catheters demonstrated a uniform, lubricious and stable (durable) coating, with a dry-out time of approximately 6 minutes. The coated catheters were then incubated in a sealed tube containing water at ambient temperature overnight (~16 hours) and re-tested. Surprisingly, the dry-out time had doubled to approximately 12 minutes, whilst still maintaining a uniform, lubricious and durable coating. Evidently, a period of extended hydration is advantageous for achieving an extended dry-out time with the coating of the invention and hence, may prove beneficial for ready-to-use (pre-hydrated) products.

The invention claimed is:
1. A coating solution which is an acidified aqueous-alcoholic solution, comprising:
(a) a poly(N-vinyl pyrrolidone-co-(meth)acrylic acid) copolymer in an amount between about 0.57% to about 6% by weight, wherein the N-vinyl pyrrolidone component of the copolymer is derived from an unsubstituted N-vinyl pyrrolidone and the (meth)acrylic component of the copolymer is derived from a substituted or unsubstituted (meth)acrylate salt, and wherein the (meth)acrylic acid component comprises from about

3% to about 35% by weight of the copolymer, calculated as weight of the corresponding (meth)acrylate sodium salt; the said copolymer having free carboxylic acid groups along the copolymer backbone, together with (b) a cross-linking agent which is capable of reacting with the carboxylic acid groups on the copolymer backbone such as to cure the copolymer, which cross-linking agent is present in the solution in an amount between about 5% and about 50% by weight relative to the copolymer; wherein the pH of the coating solution is about 4.5 or lower.

2. The coating solution according to claim 1 wherein the (meth)acrylic component is derived from one or more of acrylic acid, methacrylic acid, 2-carboxyethyl acrylate, 2-carboxyethyl methacrylate, and mono-2-(methacryloyloxy)ethyl maleate.

3. The coating solution according to claim 1 wherein the (meth)acrylic component comprises from about 5 to about 25% by weight of the copolymerised species, calculated as weight of corresponding (meth)acrylate sodium salt.

4. The coating solution according to claim 1 wherein the copolymer includes one or more additional monomer species selected from vinyl acetate, acrylamide, glycerol methacrylate, 2-hydroxethyl methacrylate, methoxy polyethylene glycol methacrylate, polyethylene glycol methacrylate, 2-methacryloyloxyethyl phosphorylcholine [2-(methacryloyloxy)ethyl]dimethyl-(3-sulfopropyl)ammonium hydroxide, 2-((2-(methacryloyloxy)ethyl)dimethylammonio)ethyl 2-methoxyethyl phosphate, and 2-((2-(methacryloyloxy)propyl)dimethylammonio)ethyl 2-methoxyethyl phosphate.

5. The coating solution according to claim 4 wherein the additional monomer species amount to not more than 40% by weight of the total copolymer.

6. The coating solution according to claim 1 wherein the alcohol diluent comprises isopropyl alcohol.

7. The coating solution according to claim 1 comprising 1 part copolymer-water mixture to 1-6 parts of alcohol, by weight.

8. The coating solution according to claim 1 wherein the cross-linking agent comprises a multifunctional carbodiimide or polycarbodiimide or aziridine or polyaziridine.

9. The coating solution according to claim 1 including one or more further hydrophilic polymers.

10. The coating solution according to claim 9 wherein the one or more further hydrophilic polymers include a hydrophilic polyurethane polymer in a weight proportion of about 1 part polyurethane to between 1.5 and 3 parts copolymer.

11. The coating solution according to claim 10 wherein the hydrophilic polyurethane polymer is present at from an equal weight to four times the weight of the cross-linking agent.

12. The coating solution according to claim 9 wherein the one or more further hydrophilic polymers include a hydrophilic polymer selected from poly(vinyl pyrrolidone), poly(ethylene glycol), poly(acrylamide), poly(vinyl alcohol), hyaluronic acid, poly(methyl vinyl ether), poly(methyl vinyl ether-alt-maleic acid), poly(methyl vinyl ether-alt-maleic anhydride), poly(acrylic acid), poly(N-vinyl pyrrolidone-co-4-benzoylphenyl methacrylate-co-methoxy polyethylene glycol methacrylate-co-butyl methacrylate), and mixtures thereof.

13. The coating solution according to claim 1 having the following composition by weight:

| | |
|---|---|
| Poly(N-vinyl pyrrolidone-co-methacrylic acid) in water: | 15-30% |
| Hydrophilic polyurethane: | 0.4-1.4% |
| Isopropyl alcohol (IPA): | 60-80% |
| Water: | 3-10% |
| Hydrophilic polymer: | 0.2-5.0% and |
| Polycarbodiimide cross-linker: | 0.15-0.5%. |

14. The coating solution according to claim 1 contained in a closed storage vessel.

15. The coating solution according to claim 1 contained in a storage vessel for at least 30 days.

16. The coating solution according to claim 1, wherein the pH of the coating solution is in the range of 3 to 4.5.

17. The coating solution according to claim 1 having the property of remaining usable for applying coatings, without further adjustment, after storage in a closed vessel for at least 30 days at a temperature not exceeding 40° C.

18. A method of coating a substrate comprising applying a coating solution according to claim 1 to a substrate, evaporating the solution to leave an uncured polymer coating thereon, and curing the coating on to the substrate.

19. A method according to claim 18, wherein the coating solution has previously been stored in a closed storage vessel for at least 30 days.

20. A method according to claim 18 wherein the coating is cured by heating in an oven or by microwave radiation.

21. A method according to claim 18, wherein the substrate is a surface of a medical device.

* * * * *